United States Patent [19]

Hankinson et al.

[11] Patent Number: 5,277,196
[45] Date of Patent: Jan. 11, 1994

[54] PORTABLE SPIROMETER WITH IMPROVED ACCURACY

[75] Inventors: John L. Hankinson, Morgantown; Joseph O. Viola, Masontown; Thomas R. Ebeling, Morgantown, all of W. Va.

[73] Assignee: The United States of America as represented by the Department of Health and Human Services, Washington, D.C.

[21] Appl. No.: 862,625

[22] Filed: Mar. 31, 1992

[51] Int. Cl.$^5$ .............................. A61B 5/08; G01F 1/86; G01F 15/02; G01F 1/68
[52] U.S. Cl. .................................. 128/725; 128/724; 73/861.03; 73/202.5; 73/204.19
[58] Field of Search ............... 128/720, 724, 725, 716; 73/861.01, 861.02, 861.03, 861.42, 202.5, 204.19

[56] References Cited

U.S. PATENT DOCUMENTS

| | | | |
|---|---|---|---|
| 3,735,752 | 5/1973 | Rodder | 128/724 |
| 4,720,800 | 1/1988 | Suzuki et al. | 73/861.03 |
| 4,815,459 | 3/1989 | Beran | 128/716 |
| 5,060,655 | 10/1991 | Rudolph | 128/716 |

OTHER PUBLICATIONS

Wright Magtrak Respiratory Monitors by fdE Ferraris Medical, Inc.
The Morgan Spirocheck Portable Spirometer.
Welch Allyn Introduces PneumoCheck.
Satellite Subminiature Spirometry System by Jones.
SpiroSense TM Spirometry System by Tamarac Systems.
Compact Spirometry by Vitalograph.

*Primary Examiner*—William E. Kamm
*Assistant Examiner*—Marianne Parker
*Attorney, Agent, or Firm*—Lowe, Price, LeBlanc & Becker

[57] ABSTRACT

A spirometric measurement device includes an arrangement for computation of a dynamic correction factor to compensate for temperature-related volume changes in time varying raw forced expiratory volume (FEV) data due to cooling of expired gas. The correction factor, which compensates for body-temperature-pressure-saturated (BTPS) changes, varies in time according to variation of temperature of a flow sensor. The temperature of the flow sensor is accurately established by positioning a temperature sensor downstream of the flow sensor.

20 Claims, 10 Drawing Sheets

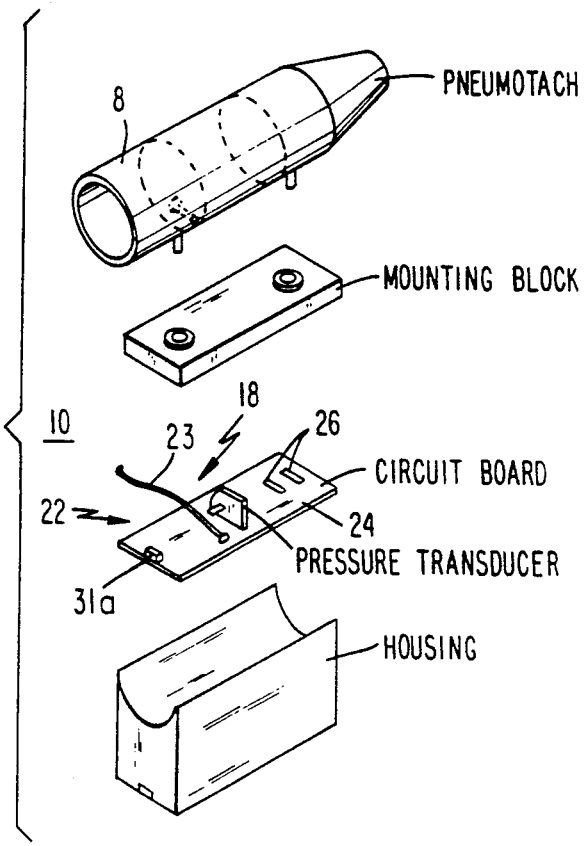
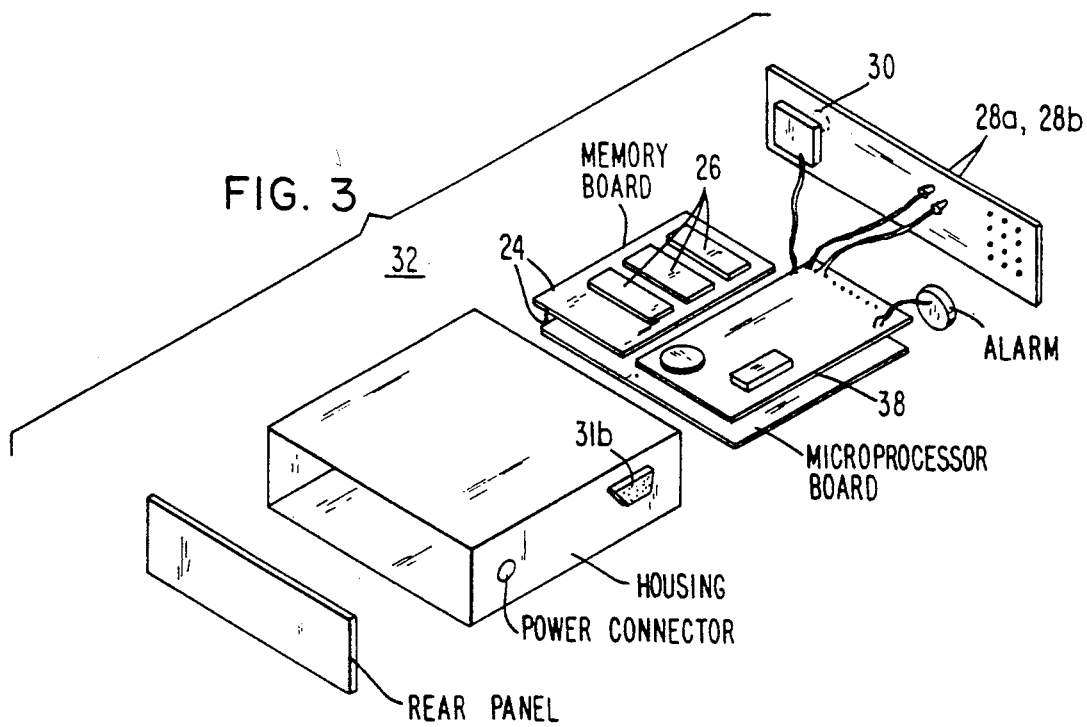

PORTABLE SPIROMETER WITH IMPROVED ACCURACY

TECHNICAL FIELD

This invention relates to spirometers, and more particularly to portable spirometers incorporating microprocessor controlled data collection devices, including non-heated ceramic flow sensors and temperature sensors for establishing a temperature correction factor for data obtained from the flow sensor.

BACKGROUND ART

Workers exposed to irritating dusts and fumes have been known to exhibit changes in lung function throughout a work shift to which they are assigned. Standard spirometry data collected before and after the work shift may detect a change in lung function from the beginning to the end of a work shift. However, it is more important to track changes in lung function and capacity on a substantially real-time, periodic basis, whether throughout the work shift or over the course of an entire day (or days).

Similarly, asthmatics may experience randomly occurring attacks. While lung function is adversely affected during the attack, lung function may return to normal thereafter. For these individuals, spirometric data collected during an attack is a more accurate representation of the nature of the attack and is thus more desirable to obtain than data indicative of lung function only at the beginning and end of an attack.

Portable, or hand held, prior art spirometric devices are commercially available. Such devices are known in the art. The known devices operate as follows.

Volume spirometers provide the simplest approach to measurement of spirometric parameters. Volume spirometers are essentially large cylindrical chambers including displaceable pistons. A test subject forces air into the chamber by performing a forced vital capacity (FVC) maneuver. The piston displacement corresponds to the volume of air being expired. Although accurate, these devices are large and bulky.

To keep the size and weight of a spirometric device to a minimum, it is known to measure flow instead of volume. Thus, in a flow-spirometer a flow sensor outputs a flow signal indicative of detected air flow thereacross. The desired volume data is then determined by mathematical integration of the flow signal. An advantage of such an approach is that flow spirometers are inherently smaller than volume spirometers. However, although implementable by a smaller device, the flow-sensing method of obtaining spirometric data is known to be less accurate and more sensitive to errors than the volume based method.

The volume of gas exhaled into both volume and flow-based spirometric devices is initially at 37 degrees C. and rapidly cools to ambient temperature. This cooling to ATPS (Atmospheric Temperature Pressue Saturated) causes a contraction of the gas from the volume occupied at BTPS (Body Temperature Pressure Saturated) in the subject's lungs. The spirometric volume measurement must therefore be multiplied by a BTPS correction factor to obtain the volume value at body temperature.

Portable flow type spirometric systems fall into one of two categories: (1) peak flow meters and (2) pneumotach systems.

Peak flow meters are very simple mechanical devices consisting of a mouthpiece and an indicator gauge. When the subject performs a FVC maneuver, the force of the expired air moves an indicating marker along a calibrated dial allowing peak flow to be read. If such a device is used without the aid of an administering technician, it is the subject's responsibility to perform the maneuver with sufficient effort, read the graduated scale correctly, and record the value along with the time of day. Peak flow is the only information that can be obtained from this type of device.

Portable pneumotach systems comprise a flow sensing pneumotach which generates an electrical flow signal proportional to flow. The flow signal is sampled periodically by a microprocessor, which then evaluates and stores the data. The flexibility of this type of device is limited by the microprocessor software, which is usually stored in a read-only-memory (ROM). It is known that different sampling programs may be needed, or provided, for different spirometric units, depending on the specific application contemplated. However, for known spirometric devices the sampling program is part of the software stored in read-only-memory (ROM). Thus, modification of the sampling (as well as other) software is not possible without disassembling the device and replacing the ROM chip.

Further, known devices fail to provide a correction factor for dynamic computation of the body-temperature-pressure-saturated (BTPS) correction factor. That is, where non-heated ceramic flow sensors are used, typically there is only incomplete cooling of the flowing air as the air passes through the sensor. Thus, the usual technique applies a factor approximately equal to thirty percent (30%) of the full BTPS CF. Upon testing of several ceramic flow sensors with a mechanical pump, using both room air and air heated to 37° C. and saturated with water vapor, the inventors discovered the following.

Upon using volume ramps and the first four ATS standard waveforms to test the sensors, and upon calculating an estimated BTPS correction for FVC and forced expiratory volume in 1 second (FEV1) by dividing the volume measured with room air by the volume measured with heated and humidified air, the results using room air showed considerable variability in the linearity of the flow sensors. One sensor showed a 400 ml difference (6.7%) in a 6 L volume ramp and flow rates of between 0.6 and 8 L/s. Using heated and humidified air, the estimated BTPS CF with the sensor initially at 20° C. ranged from 1.06 to 1.00, compared to a calculated value of 1.102. The estimated BTPS CF also varied with the number of curves previously performed, the time between curves, the volume of the current and previous curves, and the temperature of the sensor.

Thus, the known devices suffer from inaccuracies occasioned by the known technique of using ambient temperature to estimate the temperature of the flow sensor, as well as from errors arising from use of a single, static, BTPS correction factor for all parameters, without regard to the exact time that specific measurements are made during a forced exhalation and to time related temperature variation.

Additionally, known devices convert the raw spirometric data to various parameters descriptive of the user's lung capacity, storing only the resultant parameters rather than the raw data. Thus, known devices lose any capability to perform further computations on the raw data and to abstract still further information therefrom.

Moreover, known devices do not include a provision for reminding a user to obtain data periodically.

Still further, known devices suffer from inaccuracies caused by flow sensor nonlinearity and flow sensor drift.

All of the commercially available portable flow devices known to the inventors thus suffer from limitations in accuracy, flexibility, data storage capacity and physical size, and lack specific desirable options and features. The prior art devices are thus inadequate for remote and prolonged data collection.

There is accordingly a need in the prior art for a portable spirometric device capable of providing spirometric data having improved accuracy and reliability.

There is a more specific need in the prior art for a flow type spirometer including a capability for dynamic computation of the BTPS correction factor.

Still another need of the prior art is for an ability to provide actual sensor temperature values for the flow sensor of a portable spirometer.

There is a further need for a portable spirometric device having a capability for accepting different operating control programs for flexible adaptivity to various applications, including accepting differing sampling programs, without requiring disassembly or replacement of a ROM therein.

There is yet another need in the prior art, for spirometric devices including means for correcting inaccuracies caused by flow sensor nonlinearity and flow sensor drift.

Additionally, there is a need in the prior art for a portable spirometric device having improved storage capacity for raw spirometric data, to enable subsequent processing thereof.

There is moreover a need in the prior art for a portable spirometric device which periodically reminds its user to perform a FVC maneuver to obtain periodic spirometric data.

Further, there is a need in the prior art for a portable spirometric device having a reduced size to assure that a subject will not be discouraged by bulkiness of the device from carrying the device and using the spirometer as required.

DISCLOSURE OF INVENTION

It is accordingly an object of the present invention to provide a method and apparatus for acquiring pulmonary function data which meets or exceeds the standards set by the American Thoracic Society (ATS).

It is a more specific object of the invention to provide spirometric measurement apparatus which generates dynamic BTPS correction factors, thus improving accuracy and reliability of parameters computed therefrom by correction for dynamic changes in sensor and ambient air temperatures.

It is a further object of the invention to provide a spirometer including means for obtaining actual (rather than estimated) sensor temperature values for the flow sensor of a portable spirometer.

Yet another object of the invention is to provide a portable spirometric device having a capability for accepting different operating control programs for flexible adaptivity to various applications, including accepting differing sampling programs, without requiring disassembly or replacement of a ROM therein.

It is a particular object of the invention to provide a structure, such as a serial data link, for downloading programming and individual data collection features to a spirometric device from a personal computer (PC) as well as to permit the PC to retrieve and archive the spirometric data.

It is still another object of the invention to provide a spirometric device including means for correcting inaccuracies caused by flow sensor nonlinearity and flow sensor drift.

Yet another object of the invention is to provide novel software for quality control and analysis of retrieved spirometric data to insure that the data is in compliance with the ATS reproducibility and acceptability criteria.

It is another object of the invention to provide a portable spirometric device including sufficient storage capacity for raw (unprocessed) digital data to allow archiving and further analysis in scientific research.

Yet another object of the invention is to provide a spirometer capable of correctly tracking a subject's respiratory function throughout a monitored time period, by periodically reminding the subject to perform a maneuver.

It is thus a further object of the invention to provide a spirometric device having a capability of prompting a subject of a spirometric test to perform a periodic spirometry maneuver while allowing the subject to initiate the maneuver.

Still another object of the invention is the provision of a programmable alarm to prompt the subject to perform a maneuver, thus freeing the subject from both a requirement to record results and to remember when a maneuver is due.

Still a further object of the invention is to provide a spirometer including a clock for marking data representative of each maneuver with time and date information associated therewith.

It is yet another object of the invention to provide a portable spirometric device having a reduced size to assure that a subject will not be discouraged by device bulk from carrying the device and using the spirometer as required.

In accordance with another aspect of the invention, there is provided an improvement for a spirometer, which includes a temperature sensor for sensing a temperature of a flow sensor and a dynamic correction device responsive to the temperature sensor for determining a time-varying, dynamic, body-temperature-pressure-saturated (BTPS) correction factor in accordance with a time-variation in the temperature of the flow sensor sensed by the temperature sensor.

Moreover, in accordance with the invention the temperature sensor is situated at a distal end of the flow sensor and, more particularly, in a passageway downstream of the flow sensor.

In accordance with another feature of the invention, the temperature sensor outputs a time varying temperature signal representing sensor temperature as a function of time, and the dynamic correction device includes a programmed processor which is programmed to compute the dynamic BTPS correction factor as a function of the time varying temperature signals.

The programmed processor may execute a predetermined sampling program, and a separate computer, physically separate from the spirometer, may be used for storing a plurality of sampling programs. A transfer device transfers the predetermined sampling program stored in the separate computing means to the programmed processor, thereby to program the processor to execute the predetermined sampling program.

The inventive spirometer may include a timer for identifying times at which time-varying raw forced expiratory volume (FEV) data are obtained, and a storage for storing the FEV data together with the identifying times associated therewith.

Other objects, features and advantages of the present invention will become readily apparent to those skilled in the art from the following description wherein there is shown and described a preferred embodiment of the invention, simply by way of illustration and not of limitation of the best mode (and alternative embodiments) for carrying out the invention. The invention itself is set forth in the claims appended hereto. As will be realized upon examination of the specification with due reference to the drawings, the present invention is capable of still other, different, embodiments and its several details are capable of modifications in various obvious aspects, all without departing from the invention which is recited in the claims. Accordingly, the drawings and the descriptions provided herein are to be regarded as illustrative in nature and not as restrictive of the invention.

BRIEF DESCRIPTION OF THE DRAWINGS

The accompanying drawings, incorporated into and forming a part of the specification, illustrate several aspects of a preferred embodiment of the present invention and, together with the description, serve to explain the principles of the invention. In the drawings:

FIG. 2 shows an exploded view of a portable spirometric measurement device;

FIG. 3 shows an exploded view of a compartment remotely located from the portable device of FIG. 2;

BEST MODE FOR CARRYING OUT THE INVENTION

Figure 1:
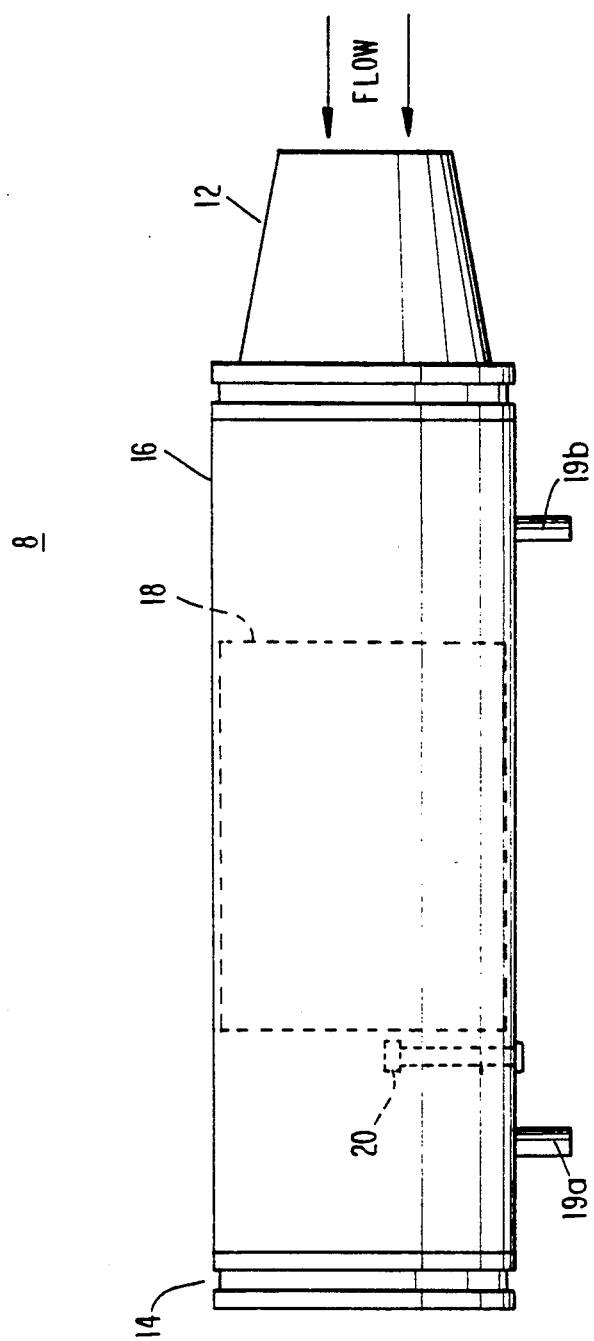
FIG. 1 illustrates an improved spirometer in accordance with the principles of the present invention.

Referring now to the drawings, there is shown in FIG. 1 an improved pneumotach 8 in accordance with the invention. The pneumotach is used in conjunction with an electronics compartment 22 to form a portable spirometric measurement device 10, shown in exploded form in FIG. 2.

As shown in FIG. 1, the pneumotach 8 includes an air inlet 12 and an air outlet 14, at respective proximal and distal ends of a passageway 16, formed by an aluminum housing. A ceramic transducer 18, of a known type, is included within the passageway. Pressure ports 19a and 19b are connected via tubing (not shown) to a pressure sensor used to generate a pressure signal indicative of the pressure drop developed across transducer 18. The pressure sensor is located within compartment 22, which is physically attached to passageway 16.

In a marked departure from the prior art, a temperature sensor 20 is positioned downstream of the sensor 18 in order to measure the temperature of the exit air. In the prior art, a temperature sensor was typically used in the electronics compartment 22, shown in FIG. 2. In the present invention, a cable 23 connects an output from the temperature sensor 20 to circuitry included in compartment 22. The inventive positioning of temperature sensor 20 is significant for the following reasons.

The inventors have discovered that, in the experiment described hereinabove, monitoring of the temperature of the air as it left the sensor, i.e., monitoring the exit temperature thereof, showed a steady rise in temperature with each successive curve. However, both the exit temperature and the estimated BTPS CF stabilized after approximately 5 curves using a particular waveform (FVC=6 L), provided there was only a short pause between curves. Use of exit air temperature alone proved to provide an effective means of estimating a dynamic BTPS CF. The use of a linear model (based on exit temperature) to estimate a dynamic BTPS CF reduced the error in FEV1 to less than ±3% for exit temperatures from 5 to 28° C.

The inventors hereof thus concluded that both sensor linearization and dynamic BTPS CF's are needed for this type of flow sensor to operate within the ATS accuracy recommendations of ±3% for FVC and FEV1, particularly at lower operating temperatures.

Accordingly, as shown in FIG. 1, in a preferred embodiment of the invention the temperature sensor 20 is located downstream (at a distal end) of the flow sensor 18 in order to provide a more accurate measurement of the exit temperature and thus to provide a more accurate representation of the transducer temperature than is available in the prior art, wherein the temperature sensor may be in a remote electronics package, or may be upstream of the transducer 18.

As is the case with known spirometers, the inventive device includes separate, interconnected, compartments 22 and 32 for electronic components. Compartment 32, hereinafter data collector 32, is remotely located from the portable device 10. An exploded view of the components of data collector 32 is shown in FIG. 3. Interconnection of compartments 22 and 32 is schematically shown in FIG. 4.

Figure 4:
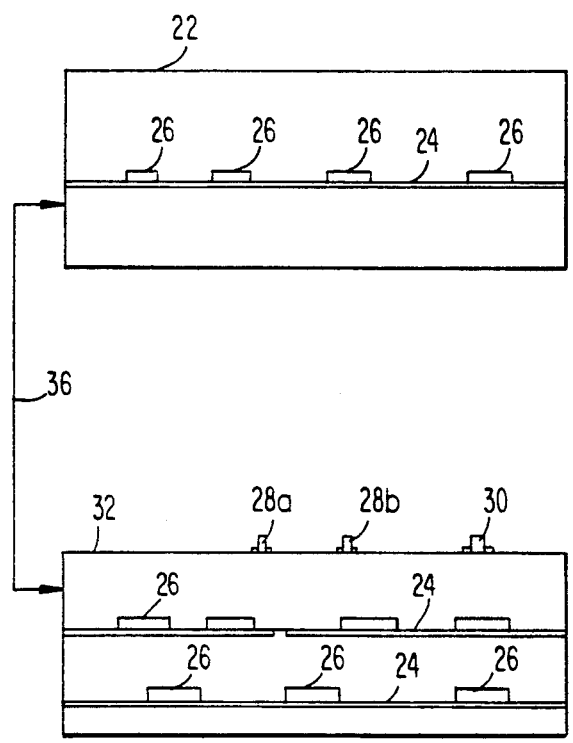
FIG. 4 schematically illustrates an interconnection of electronic compartments of FIGS. 2 and 3.

As seen in FIG. 4, internal to compartments 22 and 32 are provided one or more circuit boards 24. Mounted on these circuit boards are various integrated circuit chips 26 on which are formed various electronic components utilized in the invention, such as a microprocessor chip, an analog to digital converter (ADC) for converting analog output signals from the sensors and transducers to digital form for processing by the microprocessor, and the like. Additionally, pressure transducer 18 is included in (or is mounted on) compartment 22 for generating a pressure signal indicative of flow across transducer 18 as above described.

External to data collector 32 there are provided a pair of LED's 28a and 28b, as well as an operator activated control button, or control switch, 30. Not shown, but also available for the operator on or adjacent the exterior surface of data collector 32, are various other operator interface devices, such as a keyboard, a display, and a printing device. These devices may be used in conjunction with the inventive spirometer similarly to the use thereof in the prior art. Specific interconnections among the various elements illustrated in FIG. 4 are not shown in view of the fact that, upon reading the following disclosure, one of ordinary skill will be enabled to practice the invention by selecting among various chips, peripheral devices and interconnections therefor are known in the art.

A measurement device as hereinabove described and incorporating the inventive concept is hereinafter referenced as "uPJ".

Preferably, the uPJ is a portable spirometry system including three components. The three components, which are physically separated from each other, include: (1) the portable device 10 (including pneumotach 8), (2) a data collector 32, and (3) a personal computer (PC) 34. The pneumotach 8, which is illustrated in FIG. 1 hereof, senses the respiratory flow while the subject is performing a FVC maneuver. Flow data is sampled and stored by data collector 32 and the various electronic components thereof. The PC 34, which may be any readily available type, is initially used to program the data collector and is subsequently used to retrieve and analyze the data from the data collector.

Figure 5:
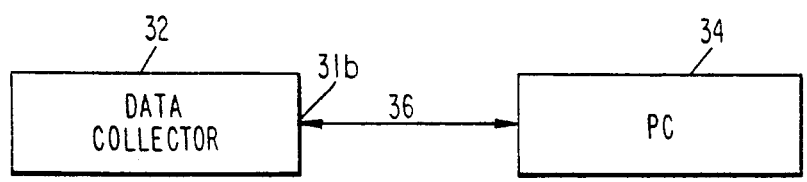
FIG. 5 shows a connection between a PC and a data collector of the invention.

The above described three components of the inventive system are first configured as shown in FIG. 5 to initialize the system. In this configuration, PC 34 is connected to the data collector 32 via a serial data cable 36. PC 34 stores a number of different sampling protocols, or programs applicable for different test conditions. Each sampling program includes specific options for administration of a spirometric test. The administering physician or technician downloads an appropriate, predetermined, sampling program from the PC 34 to data collector 32 and enters specific system/subject identifiers.

Figure 6:
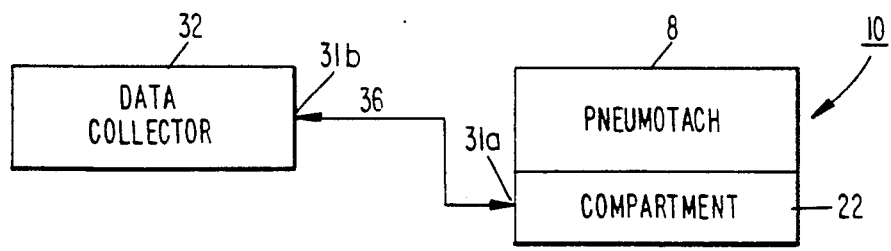
FIG. 6 illustrates a connection between the data collector and portable pneumotach components of the invention as used to collect spirometric data.

Thereafter, the PC 34 is disconnected from data collector 32 and the portable device 10 is connected thereto, as shown in FIG. 6, which illustrates a connection between the data collector and pneumotach components of the invention as used to collect spirometric data.

For ease of handling, the two components are placed in a lightweight waistpack, advantageously keeping the total system weight at less than 2.5 lbs. The subject is thus able to carry the uPJ throughout the monitoring period, performing FVC maneuvers whenever required. Operation of the system in this phase is totally controlled by the downloaded program located in the data collector. It should be appreciated that downloading of the sampling program from PC 34 to data collector 32 as shown in FIG. 5 places the program in a program random access memory (RAM) of the data collector. Thus, the control program may be changed simply and easily, by downloading a predetermined appropriate program from CPU 34 to the data collector 32, rather than requiring replacement of one ROM chip, storing one program, by a second ROM chip, storing a second program.

When data collection is completed, the system is reconnected as in FIG. 5 and the acquired data is transferred to the PC for innovative drift, temperature and quality checks, as well as for archiving, screening and analysis in accordance with standard criteria and protocols.

The portable spirometric device 10 used in the inventive uPJ system may be of a type available from Tamarac Systems of Denver, Colorado. This device requires modification to function in accordance with the invention, in order to place the temperature sensor in the pneumotach at a position downstream of the flow sensor. The Tamarac pneumotach is a totally self-contained unit which, as hereinabove described, measures flow by detecting a pressure drop developed across a ceramic screen. Analog-to-digital circuitry included in compartment 22 converts the pressure differential to a binary count. The temperature data from the sensor is digitized in a standard manner.

The temperature and pressure data are sampled at a rate of 200 samples/sec and, together, the sampled data are transmitted at 9600 baud from a port 31a of compartment 22 to a standard RS232 serial data port 31b of data collector 32. The ports are provided for communication between the electronic compartment 22 and the data collector 32. The device is arranged to receive power externally through the unused serial handshaking lines.

The Tamarac pneumotach was chosen for the inventive uPJ because the ceramic element used therein does not condense moisture, as is the case with other unheated screen sensors, thus providing a significant advantage. More specifically, moisture condensation from expired air can cause very large measurement errors by occluding the sensor screen openings. Since a large amount of electrical power must usually be dissipated to heat the sensor and evaporate such accumulated moisture, use of a non-condensing flow sensor drastically reduces the power requirement for a battery powered device.

However, from extensive experimentation with heated/humidified air as hereinabove described, the inventors herein have found that air is cooled as it passes through the ceramic element. The resulting temperature gradient can cause significant errors and is more pronounced during the first few FVC maneuvers, when the pneumotach is cool. Thus, the inventive device disclosed herein is arranged to measure the temperature of the air as it leaves the sensor, thus obtaining the exit temperature, or $T_{Exit}$. The instantaneous temperature measurement is used to calculate an appropriate dynamic BTPS CF, i.e., a correction factor which changes with time: $BTPS_{factor}(t)$.

The known method of determining the BTPS CF is to use ambient temperature to estimate sensor temperature $T_S$, and to use a single, static, value of BTPS CF for all parameters (FEV0.5, FEV1, FEV3, etc., where FEVi is the forced expiratory volume in i seconds), without regard to the time during the forced exhalation that these measurements are made. For example, in accordance with the prior art the static BTPS correction factor is determined and applied as follows:

$$BTPS_{factor} = [(BP - Vap)/(273 + T_S)]*[310/(BP-47)];$$

$$FEV1_{BTPS} = BTPS_{factor} * FEV1_{uncorrected}, \text{ or}$$

$$FEV3_{BTPS} = BTPS_{factor} * FEV3_{uncorrected}$$

(the same factor being used for FEV1 and FEV3), where:

$T_S$ = estimated sensor temperature;

BP = barometric pressure; and
Vap = Water vapor pressure at $T_S$.

Most known devices estimate the sensor temperature ($T_S$) by structuring the device to measure room temperature (temperature probe mounted inside compartment containing electronics) or sensor temperature (probe mounted at entry port to sensor), at a time immediately before the subject exhales into the device or after the forced expiration is complete. The present device measures the instantaneous exit temperature ($T_{Exit}(t)$), and uses this temperature to estimate the instantaneous sensor temperature ($T_S(t)$) according to the equation:

$$T_S(i) = -10.5 + 1.652 \cdot T_{Exit}(i) \quad (1)$$

where i = 0.5, 1, 3, etc. seconds.
Therefore for FEV0.5, the exit temperature at 0.5 seconds is measured and $$T_S(0.5) = -10.5 + 1.652 \cdot T_{Exit}(0.5).$$

In accordance with the invention, the correction factor is determined as a function of time by relying on the time dependent measured sensor temperature, using the equation:

$$BTPS_{factor}(i) = [(BP - Vap)/(273 + T_S(i))] \cdot [310/(BP - 47)]. \quad (2)$$

Thus, for 0.5 seconds, $$BTPS_{factor}(0.5) = ((BP - Vap)/(273 + T_S(0.5)) \cdot (310/(BP - 47))$$

Finally, the data for a specific time is corrected using the correction factor applicable for that time, using the following equation:

$$FEV(i)_{BTPS} = BTPS_{factor}(i) \cdot FEV(i) \quad (3)$$

Thus, to obtain corrected data for FEV0.5, the equation yields $FEV0.5_{BTPS} = BTPS_{factor}(0.5) \cdot FEV0.5_{uncorrected}$ Likewise to obtain corrected FEV1 data, the exit temperature at one second is measured and equation (1) yields $$T_S(1) = -10.5 + 1.652 \cdot T_{Exit}(1).$$

This result is used to compute the correction factor $BTPS_{factor}(0.5)$ in accordance with equation (2), from which the FEV(1) data are corrected.

It is to be noted that equation (1) used to estimate $T_S$ from $T_{Exit}$ was derived from extensive testing using heated and humidified air and a mechanical lung simulator system, as hereinabove described.

While other devices use a BTPS correction factor, none use an instantaneous BTPS(t) correction factor which is dependent on the time at which the parameter (FEV0.5, FEV1, etc.) is measured. The time dependency of the BTPS correction factor in accordance with the invention provides a significant improvement in accuracy.

As previously described herein, the prior art location of the temperature sensor in the pneumotach incorporated in the invention is internal to the electronics compartment thereof. In this location, the temperature sensor detects global changes in environmental temperature which simply fails to reflect the immediate temperature of the flow sensor or the expiratory air. By repositioning the internal temperature sensor to be adjacent (at the downstream end of) the flow sensor as shown in FIG. 1, and centering the temperature sensor in the air stream at the exhaust side of the flow sensor, temperature values at various times throughout the maneuver are measured. Thereafter, when processing the data, a dynamic BTPS correction factor is derived and applied to the data. The temperature sensor modification, together with the correcting software described below, greatly increases accuracy of the device.

Data collector 32 is used to sample the data measured by the pneumotach and communicate with a PC. Both functions are accomplished using the same serial data port 31b of a microprocessor included in the data collector. The inventive data collector utilizes an embedded microprocessor board, such as developed by and available from Triangle Digital Services of London, England under the designation TDS2020 and purchased from the Saelig Co. of Victor, NY.

Various features which are desirable for use in the inventive uPJ system, and which are found in the TDS2020 board, include:

a fast 16 bit CMOS CPU (Hitachi H8/532) running at 19.6 MHz, using an on-chip serial port and an ADC capable of digitizing 8 channels. The serial port is used to communicate with both the Tamarac (or other) pneumotach and with the PC 34 via onboard RS232 line drivers. These same drivers also supply the $\pm 8$ volts used to power the flow sensor. The A/D communication is used to monitor the battery voltage.

compact (3"×4") board structure which consumes very little power, thus allowing the data collector electronics to fit in a box measuring 1.5"×3.5"×4.5". The board typically draws 50 mA while running and less than 500 uA in sleep mode. Thus, the unit (which enters a sleep mode between maneuvers as shown in the flow chart of FIG. 6) can be powered for months from a 9 volt battery.

availability of 512 kbytes of battery-backed data RAM on board, for storing at least 128 unprocessed FVC maneuvers. A 3 volt lithium cell protects this RAM in case the main system battery fails, and an onboard real time clock to periodically time and mark the spirometry maneuvers.

Control software for the data collector 32 is described below. The software was created using a stackable development board (TDS2020DV), also purchased from Saelig. This board contains a FORTH compiler in ROM and 45 kbytes of program RAM. The software was written in FORTH on a PC and then downloaded to the TDS2020DV using the supplied development software. By keeping the development board in the final product, several sampling programs can be written and only the required version need be loaded into the data collector RAM, simplifying reconfiguration or modification of the system.

Figure 10:
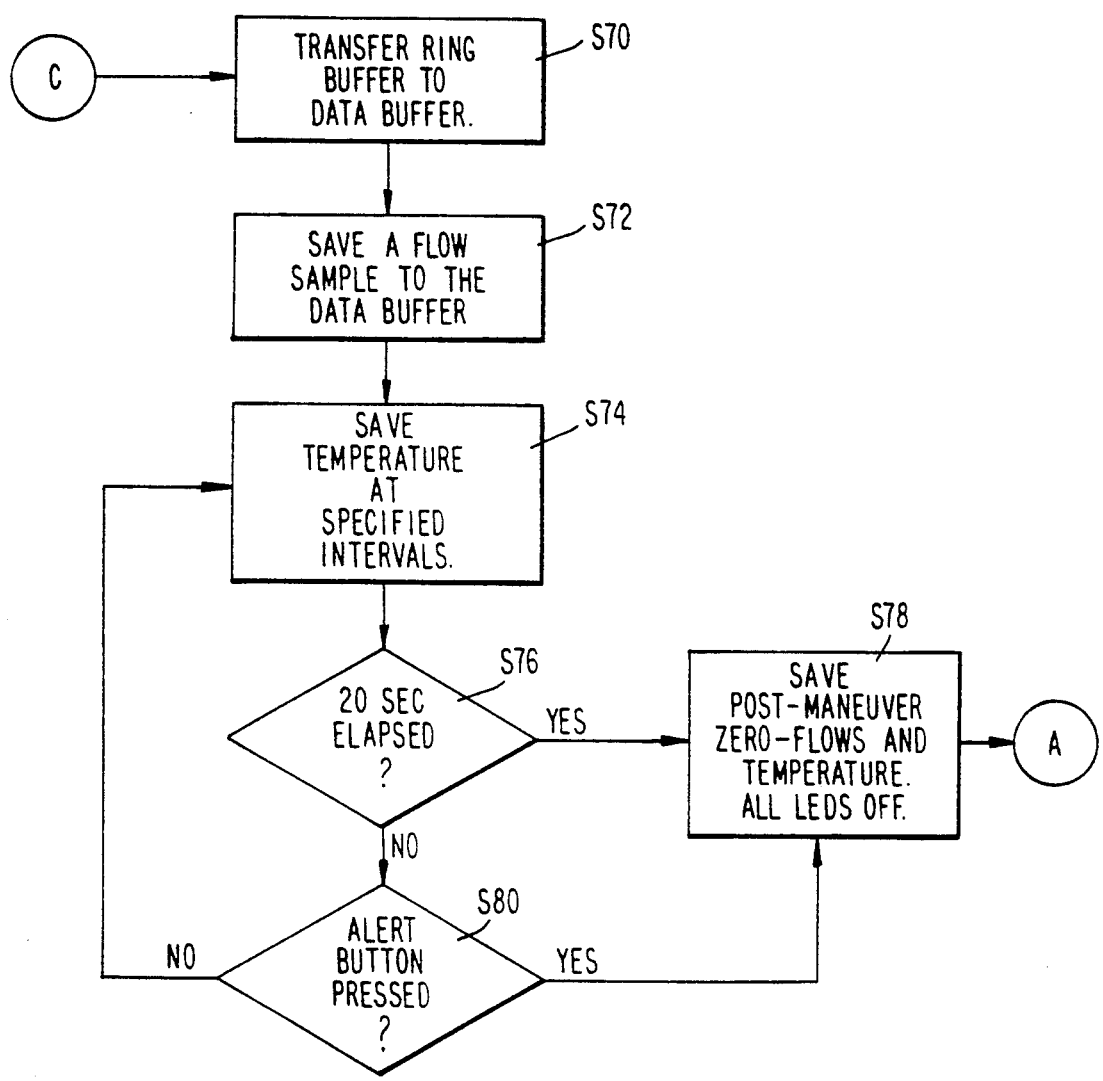
FIG. 10 shows a further flow chart for yet a further portion of the control program for the inventive device.

In addition to the two TDS boards, other components used in collecting the data includes a standard piezo alarm, used to alert the subject to perform a maneuver. Two LEDS, one red and one green, for example, are used as visible feedback to indicate when the data collector is ready to accept data and, in case of difficulty, as a system error indicator, as shown in the accompanying flow charts. Pushbutton 30 (hereinafter "alert button") is provided to allow the subject to begin a maneuver at any time, as shown in FIG. 10. Two connectors are mounted externally on the case: a standard 9-pin RS232 connector 31b and a phone plug receiving externally applied power. The additional components are routed in a known manner to a single interface board 38, and are stacked in the compartment 32 next to the TDS2020DV onto the TDS2020 board.

The personal computer 34 may be any IBM PC, laptop, or compatible computer. The computer is used to set up the data collector 32 by downloading the appropriate sampling program thereto. After data has been collected, the data is transferred to the PC for calculation and quality control. Connection to the data collector 32 is made via a standard 3-wire RS232 cable as illustrated at 36. To extend the life of the data collector system battery, external 12 volt DC power is also applied.

The following description, in conjunction with the attached flow charts, describes the software developed for the inventive system in order to enable those of ordinary skill in the art to practice the invention.

Figure 7:
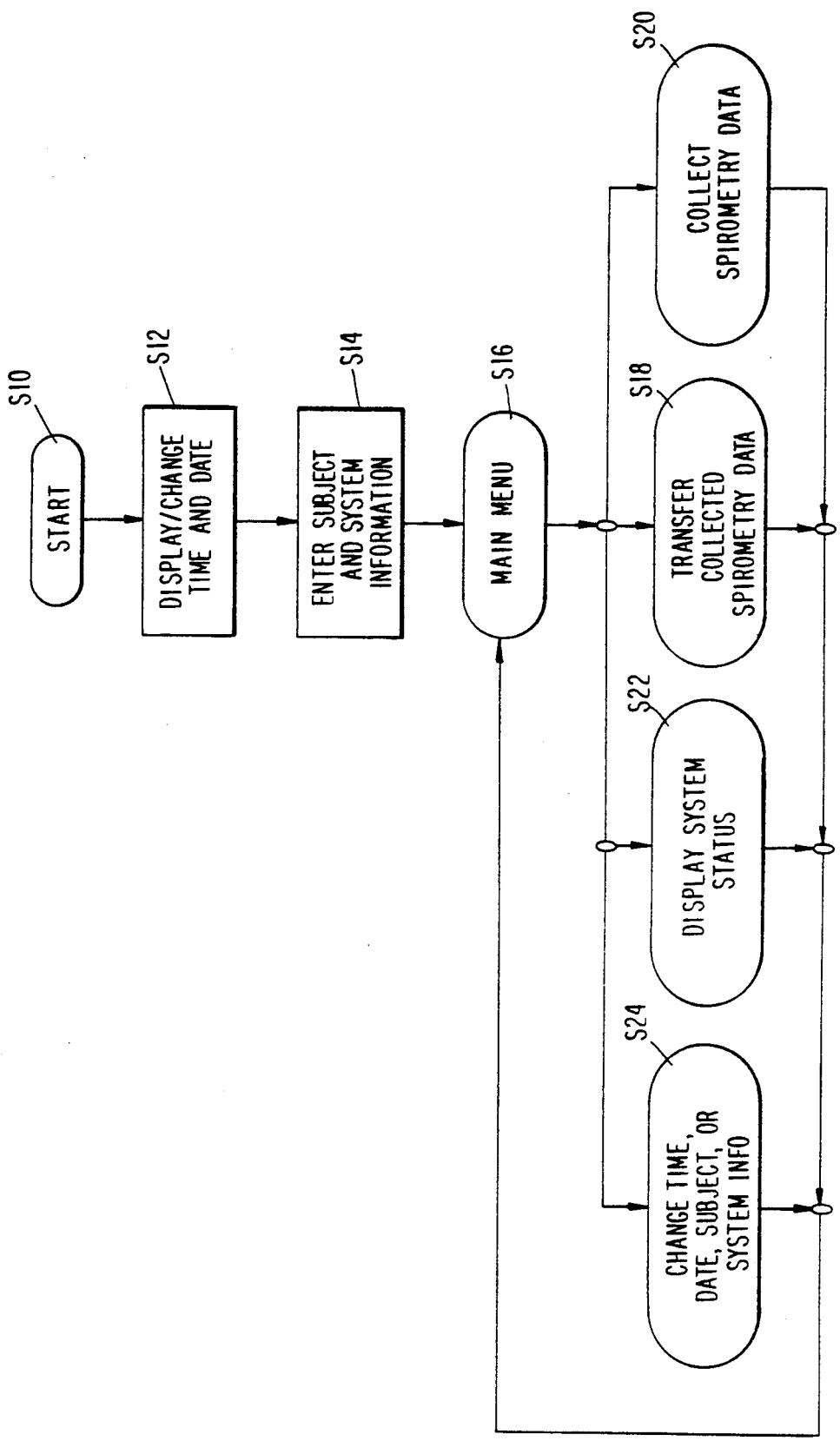
FIG. 7 is a flow chart showing a portion of a control program for the inventive device.

When power is first applied to the data collector configured in accordance with FIG. 5, the program RAM is cleared in a standard manner at step S10 in FIG. 7 and the TDS2020 is board is made ready to accept a new program. In view of the above described development used for the software, the program source code must be written in the FORTH programming language. This may be done using any PC text editor.

The FORTH source code is transferred to the data collector 32 using development software available from Triangle Digital Services under the designation TDS-PC. This software sends code, line by line, to the TDS2020 where it is compiled into program RAM. The last line of the source code must invoke its execution. The data collector now has a running program and the TDS-PC is used as a terminal emulator to communicate with the FORTH program.

A unique feature of the uPJ system is the ability to download one of several sampling programs from an IBM-PC compatible computer. This feature is an improvement over prior art devices which use software that is permanently resident in the instrument in ROM. The ability to download different sampling programs allows the same hardware to be used in different sampling environments. That is, for monitoring workers during varying work shifts (for example, alarm settings may vary) or monitoring patients with suspected asthma at home. The specific sampling program (SPIROLOG) used can therefore be varied according to the particular situation and particular conditions, and therefore allows the most appropriate and efficient means of data collection. In addition, battery usage can be minimized by entering a sleep mode as shown at step S26 in FIG. 8, thus extending the time the instrument can be used without changing the battery.

Figure 9:
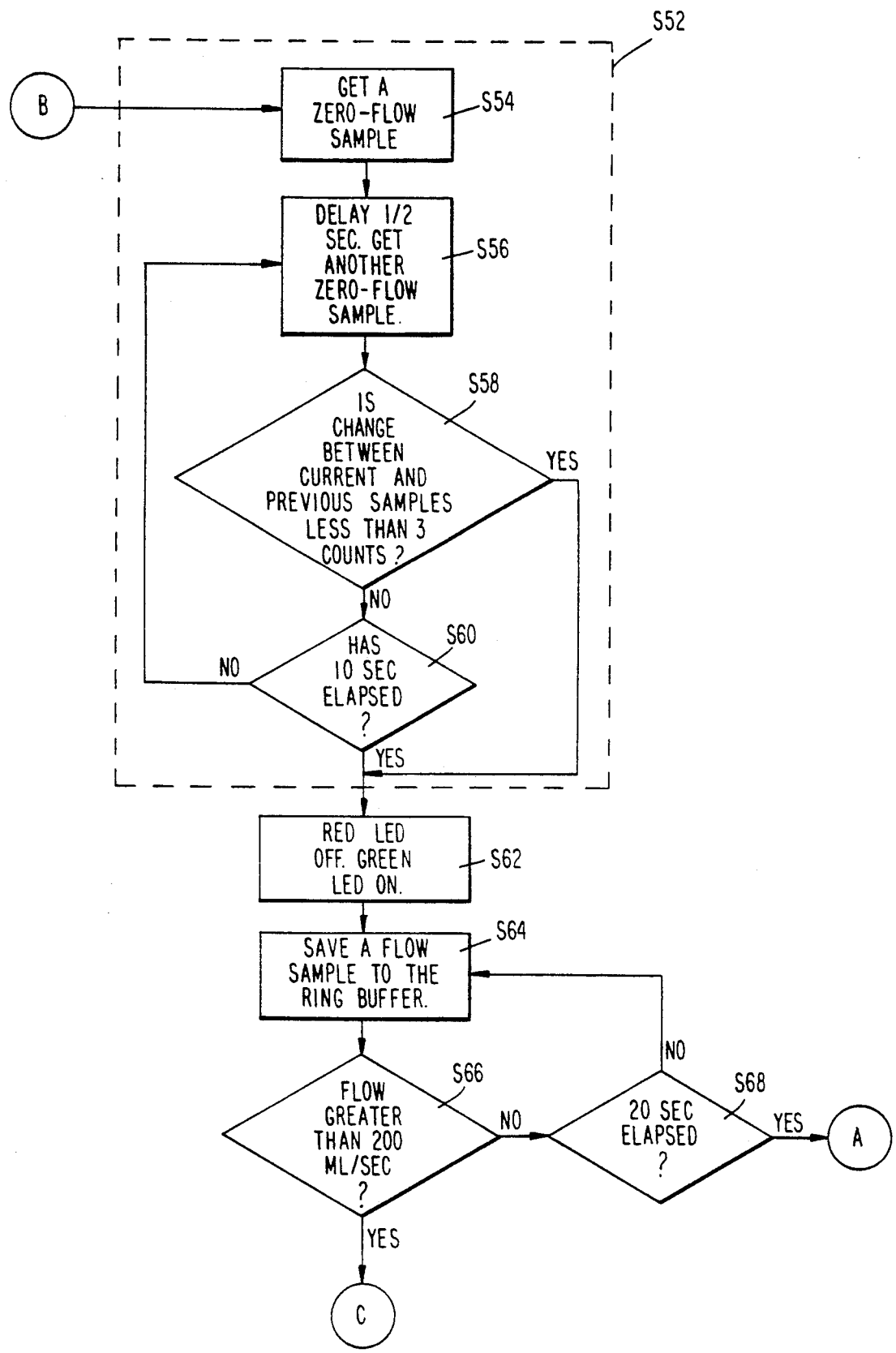
FIG. 9 is a flow chart showing a further portion of the control program.

In accordance with the invention, there is provided a sampling sequence, or program, which collects 100 FVC data points per second, for up to 20 seconds as noted at steps S62-S76 in FIGS. 9-10, after either the subject initiates a maneuver request by pressing the alert button 30 of FIG. 4, as detected at step S80 in FIG. 10, or the pre-programmed alarm has been sounded to automatically alert the subject. Without data compression, 128 flow time curves can be saved in the above noted RAM.

A different sampling program is available to compress the data if the sampling environment so dictates. Saving the entire flow time signal in RAM (as shown in steps S64 and S72) is a distinctive feature of the invention which is not available in other instruments. With the availability of the entire expiratory flow time signal, sufficient information is available to perform a thorough assessment of the maneuver's quality. In addition, sufficient information would thus be available for other software, presently being developed, to automatically classify patients as having or not having asthma.

Once SPIROLOG is running, the administering personnel is prompted by the software at steps S12 and S14 in FIG. 7 to enter the time, date, and specific patient and system parameters (i.e., subject ID, study name, etc.). After all pertinent information is collected, the SPIROLOG main menu is displayed at step S16. Here, steps S18-S24 permit the technician to view or change any entered information, begin spirometry data collection, transfer the collected data, or check the system status, such as battery voltage and number of curves collected.

Figure 8:
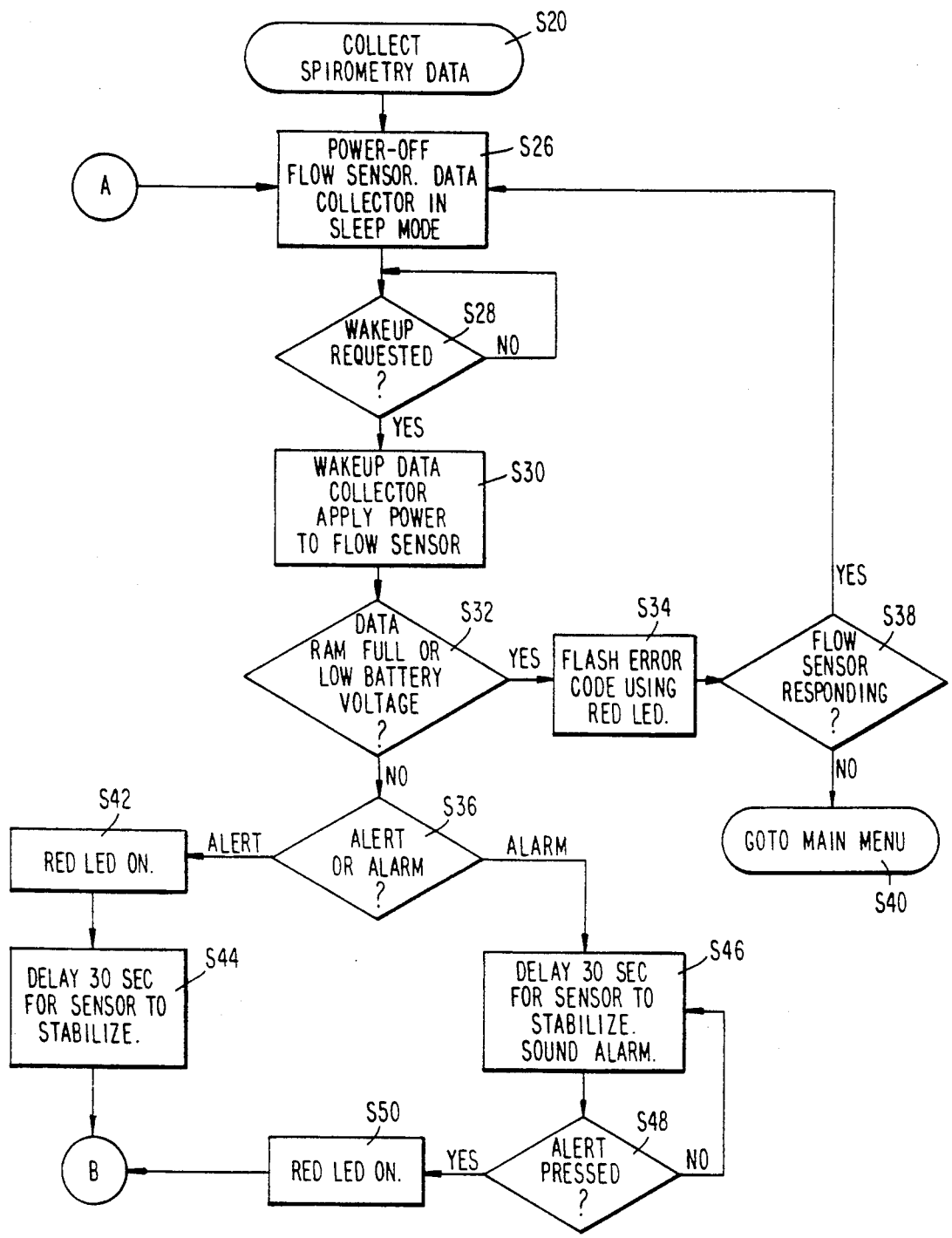
FIG. 8 is another flow chart showing another portion of the control program.

If spirometry is selected at step S20, the data collector must be disconnected from the PC and connected to the pneumotach to begin operation in accordance with the flow chart of FIG. 8. The data collector enters a sleep mode at step S26, conserving battery power. Readiness to perform a maneuver, i.e., the preprogrammed alarm has been sounded or the subject has pressed the alert button, is detected at step S28. The data collector then wakes up and applies power to the pneumotach at step S30. After some preliminary error checking at steps S32, S34 and S38 to insure the battery voltage is valid and data RAM space is available, the unit waits for the pneumotach to send flow and temperature data. When the data collector is awakened and power is applied at step S30, the device immediately begins transmitting flow and temperature data, following different sequences depending on the mode by which the device was awakened, which is determined at step S36. If data is not received within one second, it is assumed that the PC is connected and program flow is returned to the main menu, awaiting another selection from the technician. Otherwise, flow sensor data is sampled at step S64 of FIG. 9.

One of the problems with prior art pneumotachs is the tendency for the flow sensor output (or the pressure transducer output) to drift after power is first applied. A unique power-up procedure is thus provided in the present invention to help minimize this effect. As shown at steps S44 and S46 in FIG. 8, power is applied to the sensor for 30 seconds prior to actually collecting FVC data in FIG. 9. This delay is provided in order to give ample time for the amplifier electronics to stabilize to a predictable rate. In addition to this power-up delay, a pressure transducer stability test is performed prior to collecting data. The stability test is shown as a subroutine S52 in FIG. 9. This test involves sampling a zero-flow value at ½ second intervals as shown at steps S54 and S56, and comparing the current and previous values at step S58. When the difference between the two values becomes less than a predefined limit, or 10 seconds has elapsed, the subroutine exits via an affirmative determination at either of steps S58 or S60, and the green LED is turned on at step S62 to inform the subject that a maneuver may begin and that the maneuver data may be collected. This method has been found to both minimize the inherent transducer drift and to allow for accurate post-processing drift correction. On beginning the maneuver, the subject may blow into the device and sampling continues until 20 seconds of data are collected, as determined at step S76 in FIG. 10, or the subject terminates the maneuver by pressing the alert button, as established at step S80.

SPIROLOG saves the FVC data in 4096 byte blocks, as shown in Table 1 below, each containing 64 bytes of overhead and 4032 bytes (2016 integer samples) of flow data.

TABLE 1

SPIROLOG Data block format.

| Variable | # of bytes | Block byte # |
|---|---|---|
| Subject ID number | 2 | 0 |
| Study name | 8 | 2 |
| Shift code | 1 | 10 |
| Sex/Race code | 1 | 11 |
| Computer generated quality factor | 1 | 12 |
| not used | 1 | 13 |
| Temperature (C) prior to maneuver | 1 | 14 |
| Barometric pressure (mm HG-550) | 1 | 15 |
| Subject age | 1 | 16 |
| Subject height (cm) | 1 | 17 |
| Technician ID number | 2 | 18 |
| Sampling software version | 1 | 20 |
| Month at end of maneuver | 1 | 21 |
| Day at end of maneuver | 1 | 22 |
| Year at end of maneuver | 1 | 23 |
| Hour at end of maneuver | 1 | 24 |
| Minute at end of maneuver | 1 | 25 |
| Second at end of maneuver | 1 | 26 |
| Maneuver number | 1 | 27 |
| Session number | 2 | 28 |
| Data collector number | 1 | 30 |
| Data collector type | 1 | 31 |
| Pneumotach number | 2 | 32 |
| 1st Pretest 50 point flow average | 2 | 34 |
| 2nd Pretest 50 point flow average | 2 | 36 |
| 50 point flow avg 5 sec after test | 2 | 38 |
| Offset to last flow sample in block | 2 | 40 |
| Calibration syringe volume (ml) | 2 | 42 |
| 1st Posttest 50 point flow avg | 2 | 44 |
| 2nd Posttest 50 point flow avg | 2 | 46 |
| 3rd Posttest 50 point flow avg | 2 | 48 |
| Temperature count after 1 sec | 2 | 50 |
| Temperature count after 1.5 sec | 2 | 52 |
| Temperature count after 2 sec | 2 | 54 |
| Temperature count after 4 sec | 2 | 56 |
| Temperature count after 7 sec | 2 | 58 |
| Temperature count at FVC | 2 | 60 |
| Temperature count during posttest flow avgs | 2 | 62 |
| Flow data | 2 | 64-4095 |

In accordance with the preferred embodiment and in view of the constraints of the above described system, a flow sample is actually saved as a sum of two consecutive flow values, resulting in a single 10 ms sample. Also, the first 100 samples are continuously saved in a temporary (1-second) ring buffer at step S64 of FIG. 9, until a flow threshold of approximately 200 ml/sec is reached. Once reached, this one second buffer and the remaining flow samples, up to a total of 20.16 seconds, are saved to the data block at step S70 of FIG. 10. This method allows the data block to contain approximately one second of pre-maneuver data.

In addition to the raw flow samples, various zero-flow averages and temperatures are collected throughout the maneuver at steps S74 and S78. These values are used later by the PC processing software to determine the necessary correction factors in accordance with the above described equations (1), (2) and (3). Each block, therefore, contains all the information needed to accurately compute the spirometric parameters with dynamic BTPS correction.

To retrieve the spirometry maneuvers, SPIROLOG was designed to send the accumulated data blocks serially to the PC using the YMODEM transfer protocol. To do this, the data collector must be reconnected to transfer data to the PC. This may be done using any commercially available communications program, such as PROCOMM, for example. When the alert button is pressed, SPIROLOG senses the PC and returns to the main menu. The technician will then begin the data transfer at step S18, using PROCOMM or another communication program. Normally, SPIROLOG communicates to the PC at 9600 baud. However, to decrease transfer time, 38.4 kbaud is used during YMODEM transfer.

Once the raw spirometry data is transferred to the PC, several processing steps must be completed before the results are obtained. These steps are sensor linearization, sensor zero-flow correction, dynamic temperature correction, parameter calculation, and quality assessment.

Because each flow sensor has a different relationship between air flow and the pressure drop across the sensor, flow linearization is essential. To determine this correction/linearization model, a 30 point flow calibration curve is generated for each sensor by injecting constant flows from 0.4 to 12 liters per second into the sensor and measuring the corresponding pressure (flow). A very precise, hydraulic-drive mechanical pump or lung simulator is used to generate these 30 different flow rates.

Known methods fit a quadratic function to this relationship using a known least squares curve fitting technique. For this device, two spline quadratic functions are computed to model the relationship between the applied flow (derived from pump) and the resultant pressure measure by the device. Using two spline functions improves the accuracy of the device. The first quadratic function is applied for flow from 0 to 6 liters per second, and the second quadratic function is used for flows above 6 liters per second. To insure a smooth transition between 5.9 and 6.1 liter per second flow values, the second quadratic function is constrained to pass through the computed value at 6 liters per second, based on computations using the first quadratic function (spline). These functions are derived using a known constrained least squares curve fitting technique and are of the following form, easily implemented in software:

$$\text{Flow}_{corrected}(0 \text{ to } 6L/s) = B_{10} + B_{11}*\text{Pressure} + B_{12}*\text{Pressure}^2$$

$$\text{Flow}_{corrected}(>6L/s) = B_{20} + B_{21}*\text{Pressure} + B_{22}*\text{Pressure}^2$$

The coefficients $B_{ij}$ must be derived for each individual sensor.

Zero-flow correction is necessary because the pressure transducer output drifts with time. Correction consists of estimation of this drift throughout the FVC maneuver. Although this drift was found to be exponential, the SPIROLOG program delays collecting FVC data (at step S60) until the zero-flow drift has decayed to an approximate linear range (not exceeding 10 seconds). A linear drift factor is then determined from the flow before and after the maneuver. This drift correction factor is applied to each flow data point.

As previously noted herein, dynamic BTPS correction is needed to compensate for the cooling of the air as it passes through the flow sensor. The dynamic correction factor is estimated by measuring the temperature of the gas as it leaves the sensor. Through extensive testing of the sensor using heated and humidified air, a linear model was developed relating this correction factor with the exit temperature.

Figure 11:
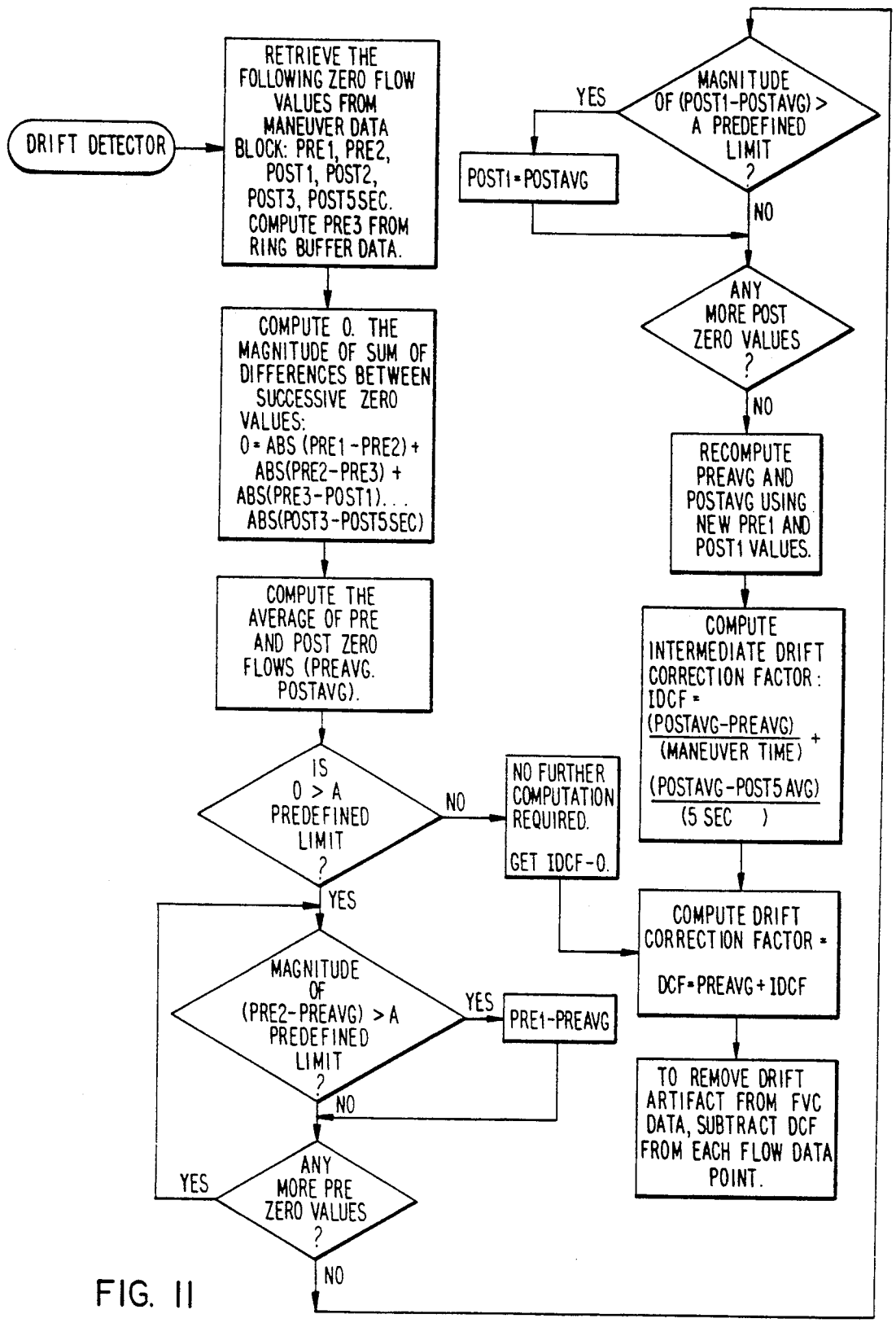
FIGS. 11-13 show flow charts for additional programs used to control operation of the inventive device.

The corrected flow signal is integrated as a function of time (volume time curve) and standard known techniques are used to calculate (PJCAL program) the following spirometric parameters:

Computer generate quality code
Peak Expiratory Flow
FVC—Forced Vital Capacity
FEV0.5—Forced Expiratory Volume in 0.5 seconds
FEV1—Forced Expiratory Volume in 1 second
FEV3—Forced Expiratory Volume in 3 seconds
FEF25-75%—Forced Expiratory Flow from 25 to 75 percent of FVC
Vext—Extrapolated Volume
$T_{tot}$—Total Expiratory time (seconds)
$T_{FVC}$—Time at which FVC was obtained In addition to the above noted calculated parameters, the parameters saved by the sampling program (SPIROLOG) are listed in Table 1, however the following parameters are of particular importance:

$T_{Zero}$—temperature before the start of the test
$T_{0.5}$—temperature at 0.5 seconds into the test
$T_1$—temperature at 1 second into the test
$T_3$—temperature at 3 seconds into the test
$T_6$—temperature at 6 seconds into the test
$T_{Eot}$—temperature at end of the test.
$T_{Post}$—temperature immediately after completion of the test The above temperatures are used to calculate a dynamic BTPS correction factor for each of the calculated parameters described above. The following pressure transducer zero values are saved for sensor zero determination and drift correction, as shown in FIG. 11. While prior devices only determine the pressure sensor zero immediately before the start of test, it will be appreciated from the sequence of steps shown in FIG. 11 that the present device measures the pressure sensor zero at several different times, both immediately before and immediately after the completion of an expiratory maneuver. These different zero pressure measurements are used to determine the sensor zero and to estimate the direction and magnitude of sensor drift. With these additional measurements, the sensor drift during the expiratory maneuver is estimated and zero correction is made for each individual flow point collected during the maneuver. Each pressure is an average pressure, averaged over a 0.5 second interval.

$P_{Zero1}$—pressure sensor zero before start of test
$P_{Zero2}$—pressure sensor zero immediately before start of test
$P_{Zero3}$—pressure sensor zero at end of test immediately before start of maneuver
$P_{Post1}$—pressure sensor zero at 0.05 seconds after end of test
$P_{Post2}$—pressure sensor zero at 0.1 seconds after end of test
$P_{Post3}$—pressure sensor zero at 0.15 seconds after end of test
$P_{Post5}$—pressure sensor zero at 5 seconds after end of test (only collected when expiratory maneuver lasts longer than 19 seconds).

The data for $P_{Post5}$ is taken when an extremely long maneuver is detected. Such a maneuver may occur either because a patient actually blows into the spirometer for that time duration, or because of sensor drift. Accordingly, the 5 second waiting period is provided to assure that the patient was not blowing into the device. Each of the post-test pressure sensor zeros ($P_{Zero3}$, $P_{Post1}$, $P_{Post2}$, $P_{Post3}$, and $P_{Post5}$) are compared to determine if they are consistent with each other. If differences between post-test pressure sensor zeros are not within limits, then an outlier routine is used to determine which value is most likely in error (different from the mean of the other values by a predetermined amount). A post-test pressure sensor zero is then determined using the average of acceptable post test pressures.

The pre-test pressure sensor zeros ($P_{Zero1}$ and $P_{Zero2}$) are compared to determine if they are within acceptable limits of each other. If they do not agree, each is compared to the average post test pressure sensor zero to determine which is most likely in error. A pre-test pressure sensor zero is then determined from the average of the pre-test pressures or the best pre-test pressure.

The direction and magnitude of the pressure sensor zero drift is calculated (PJCAL program) by computing the difference between pre and post test zero pressures versus the test time interval assuming a linear change with time. In this manner, each flow point over the entire test can be corrected for both zero pressure (flow) offset and pressure (flow) drift over the forced exhalation.

Quality assessment (PJCAL program) is performed on each maneuver to determine if it meets the American Thoracic Society's (ATS) definition of an acceptable maneuver (no excessive hesitation, cough, insufficient effort, early termination, etc). In addition, all of the maneuvers for an individual subject are compared to insure that they satisfy the ATS reproducibility criterion. While some of the methods to determine an acceptable maneuver are known (early termination), the software used with this device to detect a cough and insufficient effort is unique.

Figure 12:
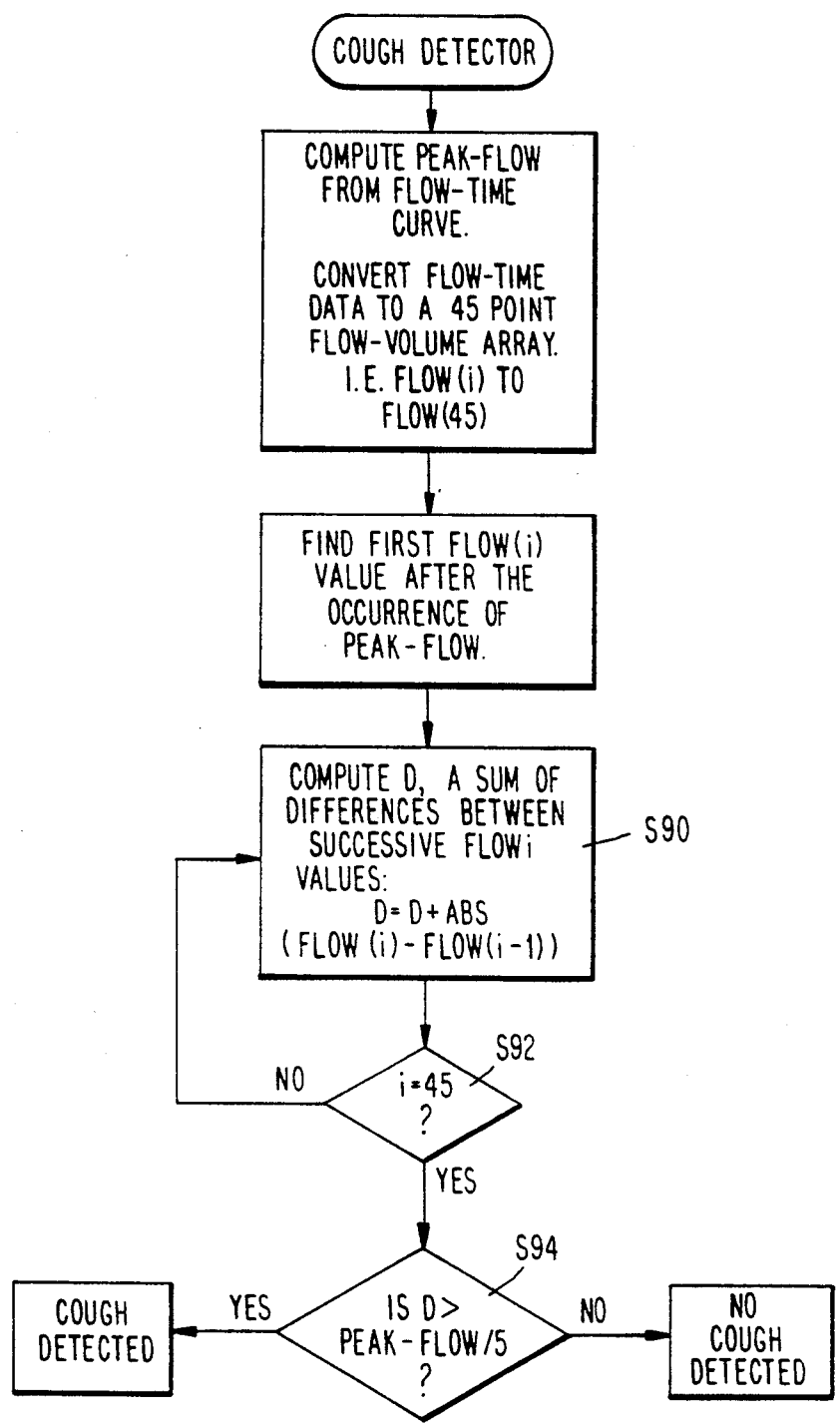

As shown in FIG. 12, a cough is detected by calculating (step S90) the first derivative of the flow with respect to volume from peak flow to the FVC ($D_i = -Flow_i / Volume_i$); where $Volume_i = i*FVC/45$ and $i = 1$ to 45 (step S92). When it is determined (step S94) that the sum of these derivatives, $D_C$, is greater than a critical threshold value (peak flow/5), then a cough is indicated.

If a cough is detected during the first second of exhalation, then this is defined as an unacceptable maneuver and this maneuver is not used. If a cough is detected after one second, then an inhalation of air during what should be a continuous forced exhalation is suspected.

Figure 13:
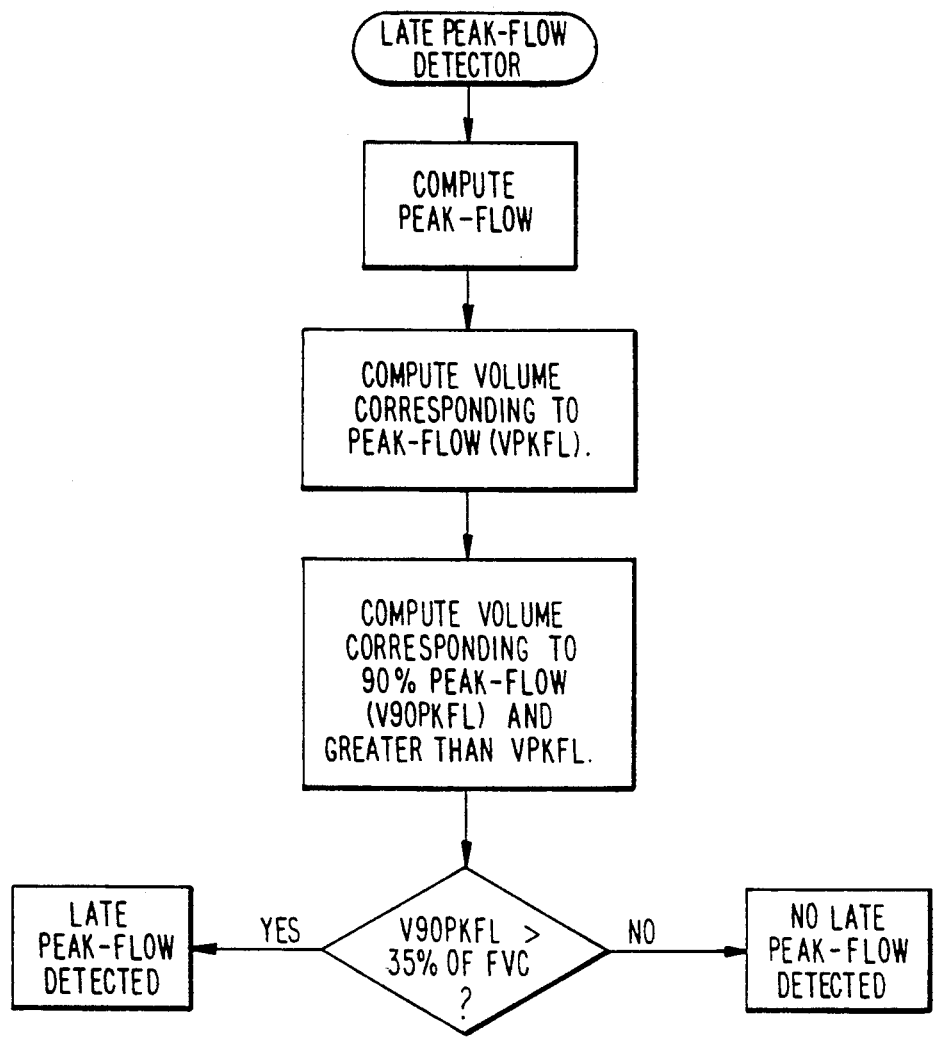

An insufficient effort is determined in accordance with the procedure shown in the flow chart of FIG. 13. Specifically, insufficient effort is determined by calculating from the flow volume curve the volume at which the value of 90 percent of peak flow (after peak flow) occurs. When this volume at which 90 percent peak flow occurs is greater than 35 percent of the FVC, a late peak flow (insufficient effort) is indicated.

After analysis in this fashion, a summary letter with test results and a medical interpretation of the results may be printed.

All of the above are accomplished using various programs written in Turbo-C and run on a PC. Other programs also exist which allow editing of the subject/system overhead data and viewing of the maneuver data in flow/volume or volume/time format.

The foregoing description of the preferred embodiments of the invention has been presented for purposes of illustration and description. It is not intended to be exhaustive or to limit the invention to the precise forms disclosed since many modifications or variations thereof are possible in light of the above teaching. All such modifications are within the scope of the invention. The embodiments described herein were chosen and described in order best to explain the principles of the invention and its practical application, thereby to enable others of ordinary skill in the art best to utilize the invention in various embodiments and with various modifications as are suited to the particular use contemplated therefor. It is intended that the scope of the invention be defined by the claims appended hereto, when interpreted in accordance with full breadth to which they are legally and equitably entitled.

We claim:

1. In a spirometer including a passageway, a flow sensor means for generating electric flow signals representing a rate of gas flow from a proximal end to a distal end of said passageway, said gas flow defining a downstream direction, and sampling means for sampling the flow signals, said flow sensor means situated between sad proximal and distal ends of said passageway, the improvement comprising:
   temperature sensing means for sensing a temperature of said flow sensor means, and
   dynamic correction means responsive to said temperature sensing means for determining a time-varying, dynamic, body-temperature-pressure-saturated (BTPS) correction factor, to compensate for temperature related volume changes in the gas in accordance with a time-variation in the temperature of said flow sensor means sensed by said temperature sensing means.

2. A spirometer as recited in claim 1, wherein said temperature sensing means is situated at a distal end of said flow sensor means.

3. A spirometer as recited in claim 1, wherein said temperature sensing means is situated in said passageway downstream of said flow sensor means.

4. A spirometer as recited in claim 1, wherein:
   said temperature sensing means outputs a time varying temperature signal representing sensor temperature as a function of time, and said dynamic correction means comprises programmed processing means, said programmed processing means programmed to compute said dynamic BTPS correction factor as a function of said time varying temperature signal.

5. A spirometer as recited in claim 4, wherein said programmed processing means is further programmed to correct time-varying raw forced expiratory volume (FEV) data by dynamically applying said dynamic BTPS correction factor thereto.

6. A spirometer as recited in claim 5, further comprising timing means for identifying times at which said time-varying raw FEV data are obtained, wherein said programmed processing means further comprises storage means for storing corrected FEV data.

7. A spirometer as recited in claim 1 wherein said sampling means comprises programmed processing means for executing a predetermined sampling program, separate computing means physically separate from said spirometer and storing a plurality of sampling programs therein, and transfer means for transferring said predetermined sampling program stored in said separate computing means to said programmed processing means thereby to program said programmed processing means to execute said predetermined sampling program.

8. A spirometer as recited in claim 7 wherein said programmed processing means comprises a serial communication port and said transfer means comprises communication means connected between said separate computing means and said serial communication port of said programmed processing means for transferring said predetermined sampling program to said serial communication port.

9. A spirometer as recited in claim 8, wherein:
   said temperature sensing means outputs a time varying temperature signal representing sensor temperature as a function of time, and said dynamic correction means is included in said programmed processing means,
   further including additional processing means programmed to compute said dynamic BTPS correction factor as a time varying function of said time varying temperature signal,
   said additional processing means being further programmed to correct time-varying raw forced expiratory volume (FEV) data by dynamically applying said dynamic BTPS correction factor thereto,
   further comprising timing means for identifying times at which said time-varying raw FEV data are obtained, and
   storage means for storing corrected FEV data.

10. A spirometer as recited in claim 9, further comprising annunciating means responsive to said timing means for prompting a subject of a forced vital capacity (FVC) maneuver to initiate a FVC maneuver using said spirometer.

11. A spirometer as recited in claim 7, wherein said programmed processing means further comprises storage means for storing time-varying raw forced expiratory volume (FEV) data, said transfer means operating subsequent to a forced vital capacity (FVC) maneuver to transfer stored FEV data from said programmed processing means to said separate computing means for processing and archival storage.

12. A spirometer as recited in claim 7, wherein said programmed processing means is further programmed for correcting inaccuracies caused by flow sensor non-linearity and flow sensor drift.

13. A spirometer as recited in claim 1, further comprising timing means for identifying times at which time-varying raw forced expiratory volume (FEV) data are obtained,
   storage means for storing said FEV data together with said identifying times associated therewith.

14. A spirometer as recited in claim 13, further comprising annunciating means responsive to said timing means for prompting a subject of a forced vital capacity (FVC) maneuver to initiate a FVC maneuver using said spirometer.

15. A spirometer as recited in claim 1, wherein said dynamic correction means comprises programmed processing means,
   said programmed processing means programmed for processing samples of said flow signals provided by said sampling means for determining acceptability of the samples.

16. A spirometer as recited in claim 15, wherein said programmed processing means is programmed to detect insufficient effort by a subject using the spirometer.

17. A spirometer as recited in claim 15, wherein said programmed processing means is programmed for detecting a cough by a subject using the spirometer.

18. In a spirometer including a passageway, a flow sensor means for generating electric flow signals representing a rate of gas flow from a proximal end to a distal end of said passageway, said gas flow defining a downstream direction, and sampling means for sampling the flow signals to provide time varying forced expiratory volume (FEV) data, said flow sensor means situated between said proximal and distal ends of said passageway, the improvement comprising:

temperature sensing means for sensing a temperature of said flow sensor means, said temperature sensing means situated in said passageway downstream of said flow sensor means, and programmed processing means programmed to compute a body-temperature-pressure-saturated (BTPS) correction factor, to compensate for temperature related volume changes in the gas in accordance with the temperature of said flow sensor means sensed by said temperature sensing means.

19. A spirometer as recited in claim 18, wherein said programmed processing means further comprises storage means for storing said FEV data sampled by said sampling means.

20. A spirometer are recited in claim 19, further comprising separate computing means physically separate from said spirometer and transfer means connecting said separate computing means and said programmed processing means for transferring stored FEV data from said programmed processing means to said separate computing means for processing and archival storage.

* * * * *